(12) United States Patent
Min et al.

(10) Patent No.: US 7,363,077 B1
(45) Date of Patent: Apr. 22, 2008

(54) ADAPTIVE TIMING INTERVAL CONTROL METHOD FOR TREATING CONGESTIVE HEART FAILURE

(75) Inventors: Xiaoyi Min, Thousand Oaks, CA (US); Gene A. Bornzin, Simi Valley, CA (US)

(73) Assignee: Pacesetters, Inc., Sylmar, CA (US)

( * ) Notice: Subject to any disclaimer, the term of this patent is extended or adjusted under 35 U.S.C. 154(b) by 299 days.

(21) Appl. No.: 10/986,010

(22) Filed: Nov. 9, 2004

(51) Int. Cl.
*A61N 1/362* (2006.01)
*A61N 1/37* (2006.01)

(52) U.S. Cl. .............................. 607/9; 607/23; 607/24

(58) Field of Classification Search ................ 600/508, 600/510, 513, 526; 607/2, 9, 17, 18, 23, 607/24
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,334,222 A | 8/1994 | Salo et al. | 607/17 |
| 5,466,254 A | 11/1995 | Helland | 607/123 |
| 5,476,483 A | 12/1995 | Bornzin et al. | 607/17 |
| 5,549,650 A | 8/1996 | Bornzin et al. | 607/24 |
| 5,584,868 A | 12/1996 | Salo et al. | 607/17 |
| 5,626,623 A | 5/1997 | Kieval et al. | 607/23 |
| 5,643,327 A | 7/1997 | Dawson et al. | 607/24 |
| 6,144,880 A | 11/2000 | Ding et al. | 607/23 |
| 6,314,323 B1 | 11/2001 | Ekwall | 607/23 |
| 6,351,673 B1 | 2/2002 | Ding et al. | 607/24 |
| 6,360,127 B1 | 3/2002 | Ding et al. | 607/23 |
| 6,507,756 B1* | 1/2003 | Heynen et al. | 607/9 |
| 6,810,284 B1* | 10/2004 | Bradley | 600/510 |
| 2002/0049478 A1 | 4/2002 | Ding et al. | 607/17 |
| 2002/0161307 A1 | 10/2002 | Yu et al. | 600/509 |
| 2003/0018363 A1 | 1/2003 | Ding et al. | 607/9 |
| 2003/0055462 A1 | 3/2003 | Lidman et al. | 607/25 |
| 2003/0097158 A1 | 5/2003 | Belalcazar | 607/32 |
| 2003/0144702 A1 | 7/2003 | Yu et al. | 607/17 |
| 2003/0144703 A1 | 7/2003 | Yu et al. | 607/17 |
| 2004/0030356 A1 | 2/2004 | Osypka | 607/17 |
| 2004/0254483 A1* | 12/2004 | Zdeblick et al. | 600/486 |
| 2005/0149137 A1* | 7/2005 | Chinchoy et al. | 607/25 |

FOREIGN PATENT DOCUMENTS

| | | |
|---|---|---|
| EP | 1 350 539 A1 | 10/2003 |
| WO | WO 97/40884 | 6/1997 |
| WO | WO 99/58191 | 11/1999 |
| WO | WO 01/76686 A2 | 10/2001 |
| WO | WO 01/76686 A3 | 10/2001 |
| WO | WO 03/037428 A2 | 5/2003 |
| WO | WO 03/092804 | 11/2003 |

* cited by examiner

*Primary Examiner*—Kennedy J. Schaetzle
*Assistant Examiner*—Natasha Patel

(57) ABSTRACT

A method of treating a heart with an implantable cardiac stimulation device involves transiently disturbing the steady state hemodynamic parameters by altering a cardiac cycle timing interval sufficient to reduce end diastolic volume for that cycle. The cardiac cycle timing interval is then adaptively controlled for successive cardiac cycles to achieve a second set of hemodynamic parameters.

18 Claims, 6 Drawing Sheets

ADAPTIVE TIMING INTERVAL CONTROL METHOD FOR TREATING CONGESTIVE HEART FAILURE

FIELD

The following relates generally to cardiac stimulation devices, and more particularly to methods employed by cardiac stimulation devices to treat congestive heart failure.

BACKGROUND

Congestive heart failure is a serious condition that affects the pumping ability of the heart. The condition often manifests itself within the cardiac cycle as an abnormal diastole phase (diastolic heart failure) or systole phase (systolic heart failure).

Diastolic heart failure (DHF) often involves an abnormally slow relaxation of the heart muscle during diastole, and a high peaking pressure. This peaking pressure is often referred to as afterload. The left ventricle may become stiff and non-compliant, thus inhibiting easy filling with the available filling pressure, or "preload." Consequently, in order to achieve a given volume, more pressure is needed. This, in turn, causes the heart to work harder. Ultimately, diastolic heart failure leads to systolic heart failure.

Generally, systolic heart failure (SHF) involves an abnormally large resting volume. The larger volume corresponds to increased heart wall tension or strain, thinner heart walls, and other related problems that lead to tissue damage. A positive destructive feedback loop often develops, resulting eventually in total cardiac failure.

As an aid in understanding diastolic and systolic heart failure, pressure-volume (PV) loops for the left ventricle of 1) a healthy heart, 2) a heart experiencing systolic heart failure, and 3) a heart experiencing diastolic heart failure are illustrated as superimposed graphs in FIG. 1.

During the filling portion, represented by the segments a, a' and a", the DHF and SHF segments exhibit an increase in pressure as the volume increases. In contrast, the normal heart pressure remains relatively constant. For the isovolumetric contraction segment b, b' and b", the volume stays relatively constant for all three curves while the pressure spikes as the heart contracts. As the heart ends systole and goes through the ventricular ejection segment c, c', c", the pressure in the normal heart remains relatively constant with decreasing volume, while significant pressure drops are exhibited by the SHF and DHF curves. During the last component of the cycle, the pressure drops to a minimal filling level as volume is minimized.

In addition to the individual curve segment differences between the normal heart, and DHF and SHF, significant overall shifts in the curves are apparent. For DHF, the curve (as shown by segments a", b", c" and d") exhibits a distinctive upward pressure shift, and a more constrained range in volume (beginning higher than normal at the start of the cycle, but maximizing at a value less than normal). The SHF curve (a', b', c; and d') exhibits a more pronounced shift outward in volume and a more constrained pressure range.

Conventional methods of treating congestive heart failure typically focus on drug therapy and lifestyle changes. Pacing therapy has also been employed through the use of implantable cardiac stimulation devices. These devices, such as pacemakers, implantable cardioverter defibrillators (ICD's) or cardiac resynchronization therapy devices (CRT), typically monitor cardiac arrhythmias, and in most cases, provide a form of electrical stimulation therapy to the heart as needed. Modern electronics have enabled the miniaturization of these devices for implantation in a patient for constant monitoring.

One proposed method for optimizing the hemodynamic parameters for a heart in CHF using an implantable cardiac device monitors and adjusts the atrioventricular delay (AV delay) for the heart in an effort to optimize hemodynamics during steady state. While this approach appears beneficial for its intended purpose, it does not suggest how to reverse the detrimental remodeling caused by CHF as shown in FIG. 1.

What would be desirable is a method of shifting the P-V loop curve for a heart experiencing congestive heart failure to a more normal curve with corresponding improvements in the heart's hemodynamic parameters.

SUMMARY

The adaptive system and method described herein provide a unique way to treat congestive heart failure with an implantable cardiac stimulation device. Over time, the method results in a shifting of the PV loop to a more normal operating state. The method and system are operative to treat either DHF or SHF, since both DHF and SHF exhibit excessive end diastolic volumes.

To realize the foregoing advantages, in one embodiment a method of treating a heart with an implantable cardiac stimulation device is disclosed. The method involves transiently disturbing the steady state hemodynamic parameters by altering a cardiac pacing timing interval by an amount sufficient to reduce end diastolic volume for that cycle. The altered timing interval may be used for one cycle or multiple cycles. In one embodiment, the cardiac pacing timing interval is then adaptively controlled for successive cardiac cycles to achieve a second set of hemodynamic parameters.

In another embodiment, an implantable cardiac stimulation device for treating a heart suffering from congestive heart failure is disclosed. The device comprises means for disturbing the steady state hemodynamic parameters by altering a cardiac pacing timing interval sufficient to reduce end diastolic volume for that cycle. Additionally, means for adaptively controlling the cardiac pacing timing interval for successive cardiac cycles is provided to achieve a second set of hemodynamic parameters.

Other features and advantages will be apparent from the following detailed description when read in conjunction with the accompanying drawings.

BRIEF DESCRIPTION OF THE DRAWINGS

The various features of the adaptive timing interval control method and the manner of attaining them will be described in greater detail with reference to the following description, claims, and drawings, wherein reference numerals are reused, where appropriate, to indicate a correspondence between the referenced items, and wherein:

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As described above, a unique adaptive timing interval control method is provided for reducing end diastolic volume to treat congestive heart failure. The method is carried out by an implantable cardiac stimulation device, over the long term, to reverse the effects of remodeling caused by congestive heart failure.

The techniques described below are intended to be implemented in connection with any stimulation device that is configured or configurable to stimulate nerves and/or stimulate and/or shock a patient's heart.

Figure 1:
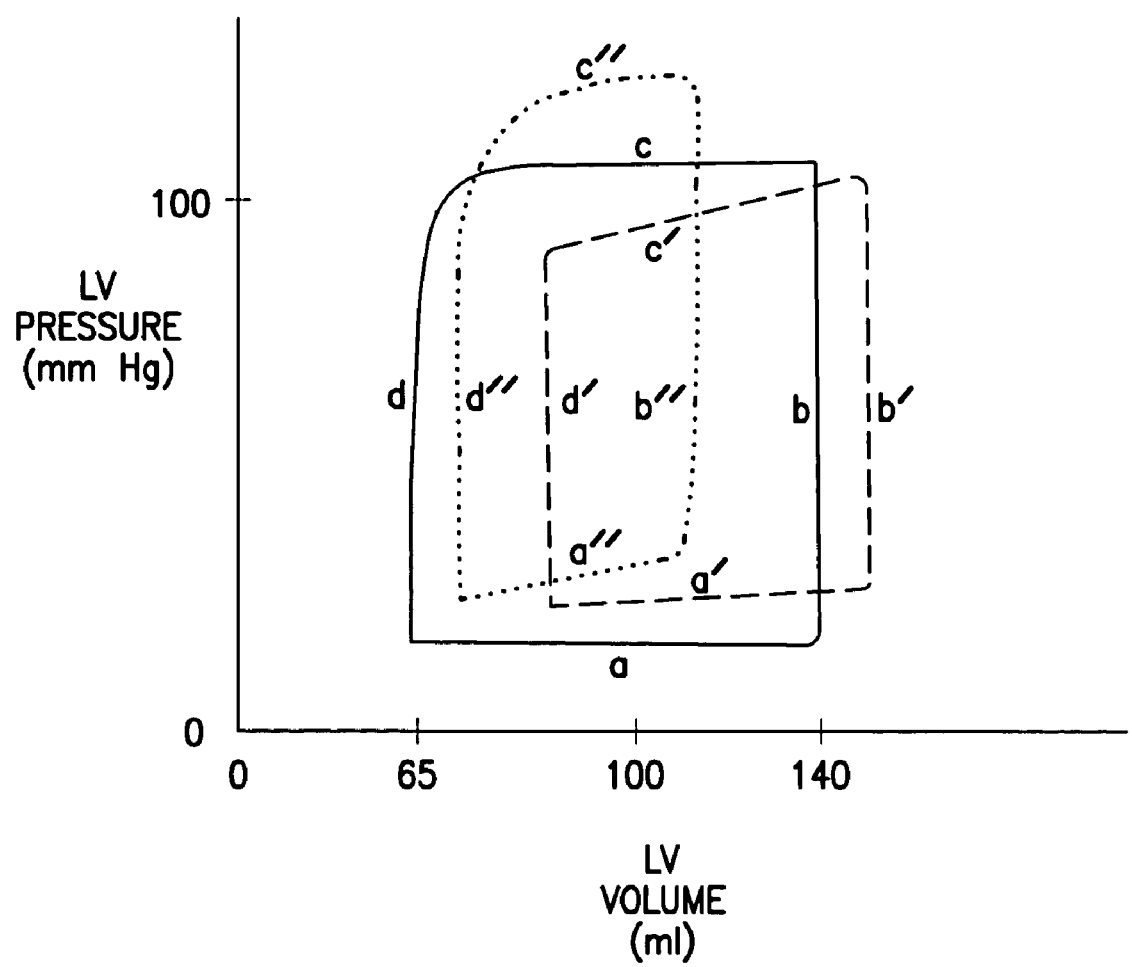
FIG. 1 is a graphical representation of a plurality of PV loops superimposed on one scale to illustrate the relative PV shifts due to congestive heart failure.
Figure 2:
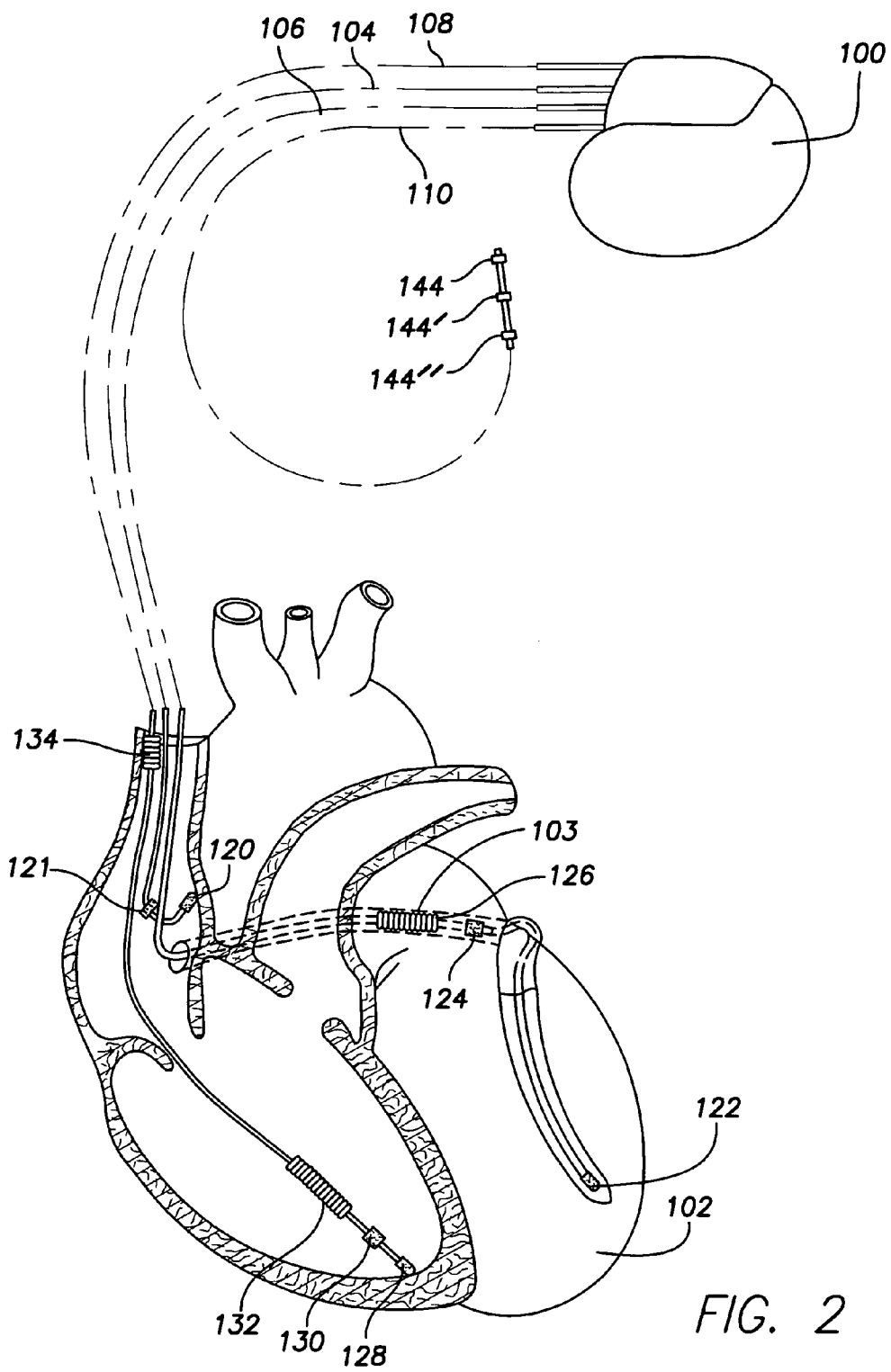
FIG. 2 is a simplified diagram illustrating an implantable stimulation device in electrical communication with at least three leads implanted into a patients heart for delivering multi-chamber stimulation and shock therapy.

FIG. 2 shows an exemplary stimulation device 100 in electrical communication with a patient's heart 102 by way of three leads 104, 106, 108, suitable for delivering multichamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 2, the stimulation device 100 is coupled to an implantable right atrial lead 104 having, for example, an atrial tip electrode 120, which typically is implanted in the patient's right atrial appendage. The lead 104, as shown in FIG. 2, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 3:
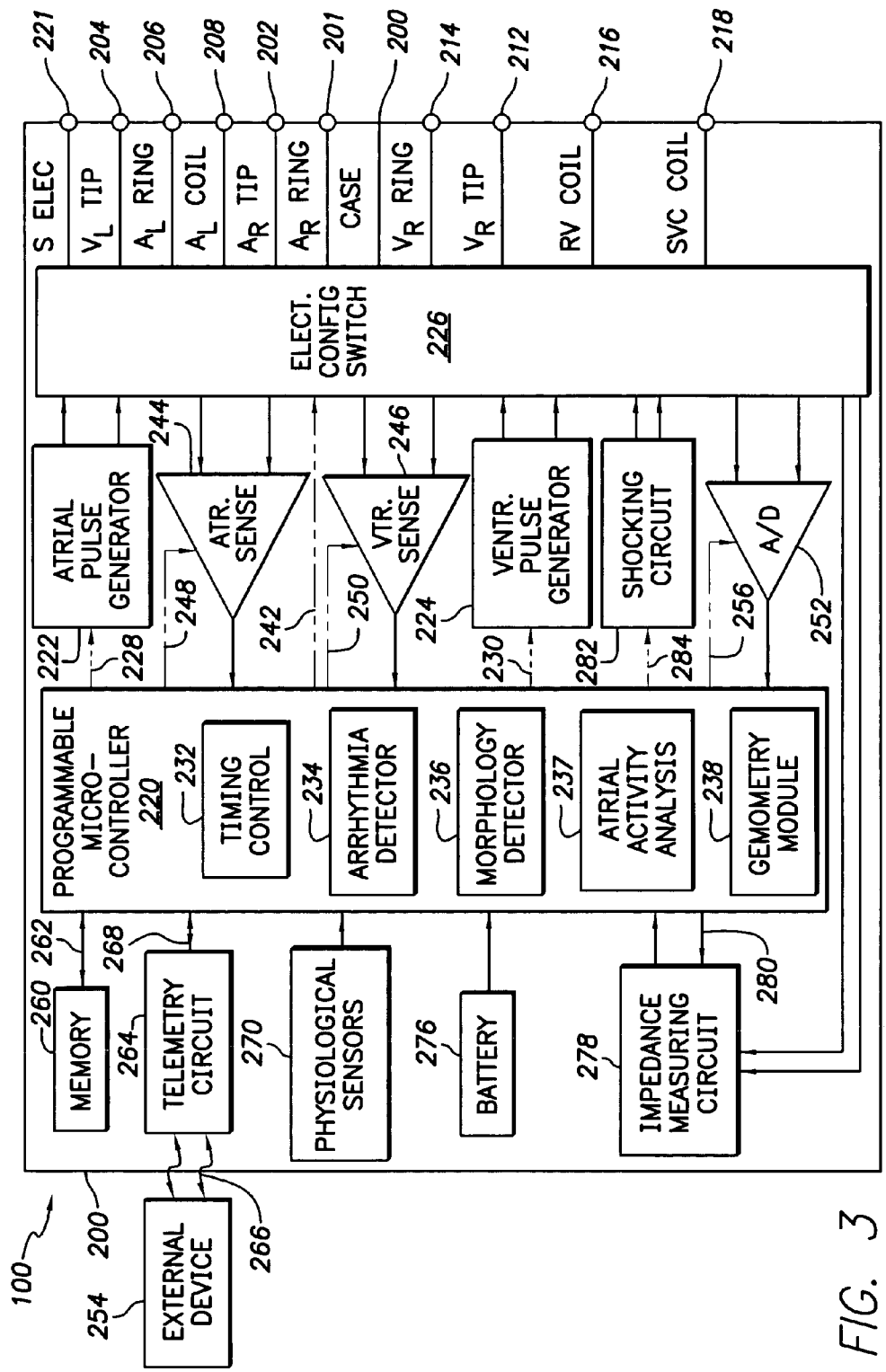
FIG. 3 is a functional block diagram of a multi-chamber implantable stimulation device illustrating the basic elements of a stimulation device that can provide cardioversion, defibrillation and pacing stimulation in four chambers of the heart.

FIG. 3 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes.

Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 3 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses. Further detail regarding a preferred driver architecture that provides maximum flexibility for reconfiguring electrode polarities and stimulus sites is described below.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 3. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled, for example, to the right atrial lead 104, the coronary sinus lead 106, and/or the right ventricular lead 108 through the switch 226 to sample signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Implantable hemodynamic monitors (IHMs) may also be employed. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 3. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

For patients diagnosed with congestive heart failure, the implantable cardiac stimulation device described above is especially suited for carrying out a method to dynamically change the heart's hemodynamic system parameters. This, in turn, corresponds to a shift in the P-V loop curve to a more normal steady state. Over time the changes in steady state promote reversal of the heart failure condition.

Figure 4:
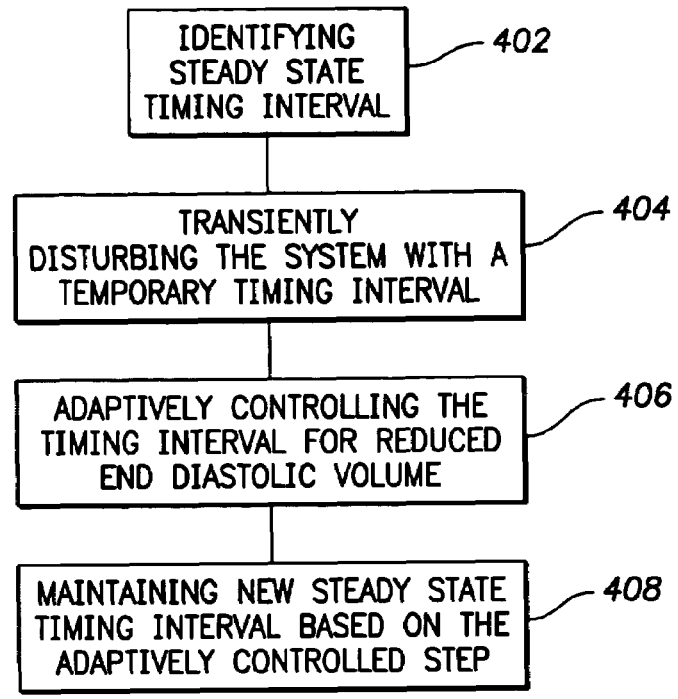
FIG. 4 is a flowchart illustrating high-level steps employed to carry out one form of the adaptive timing control method described herein.

At a high level, and referring to FIG. 4, the method involves identifying the existing steady state timing interval of interest, at step 402. For example, the timing interval may be the A-V or P-V delay (hereinafer referred to collectively as "A-V delay"), an interatrial delay (A-A delay), interventricular delay (V-V delay) or pacing rate (timed from atrial events or ventricular events). The system is then transiently disturbed, at step 404, by a temporary timing interval generated by the cardiac stimulation device. In one embodiment, the A-V or P-V delay is changed from its steady state value (e.g., 200 milliseconds) to a shortened, temporary value (e.g., 120 milliseconds) for one or more cardiac cycles. The shortened A-V delay results in reduced filling times for the ventricles, and therefore a reduction in end diastolic volume.

In one embodiment, a minimum value for the P-V delay may be set by the device, for example 50 milliseconds, and likewise a minimum value for the A-V delay may be set, for example 80 milliseconds. Thus the transient disturbance would not be any shorter than a 50 millisecond P-V delay or an 80 millisecond A-V delay. It will be understood that the A-V and P-V delays may also have maximum values, for example that may be dictated by the intrinsic conduction delay (i.e., the maximum values for A-V and P-V should be shorter than the intrinsic conduction delays).

The timing interval is then adjusted, at step 406, to a steady state value. In one embodiment, shown in FIGS. 6A and 6B, the timing interval is stepped to a new value $TI_{NEW}$; alternatively, the timing interval may be returned to the initial value. In either case the steady state timing interval is maintained, at step 408. The above-described method may be performed periodically, for example hourly, daily, weekly, etc.

We have found that by altering the timing intervals of events that reduce end diastolic volume (EDV) through pacing therapy, changing the hemodynamic steady state may be controlled in an adaptive manner. Suitable timing intervals include the delay between atrial and ventricular events (A-V delay), the period between subsequent atrial events (A-A interval), the period between successive ventricular events (V-V interval), the delay between a ventricular event and a subsequent atrial event (V-A interval), heart rate, intentional injection of PVCs, and any other suitable events that reduce ventricular filling times.

Figure 5:
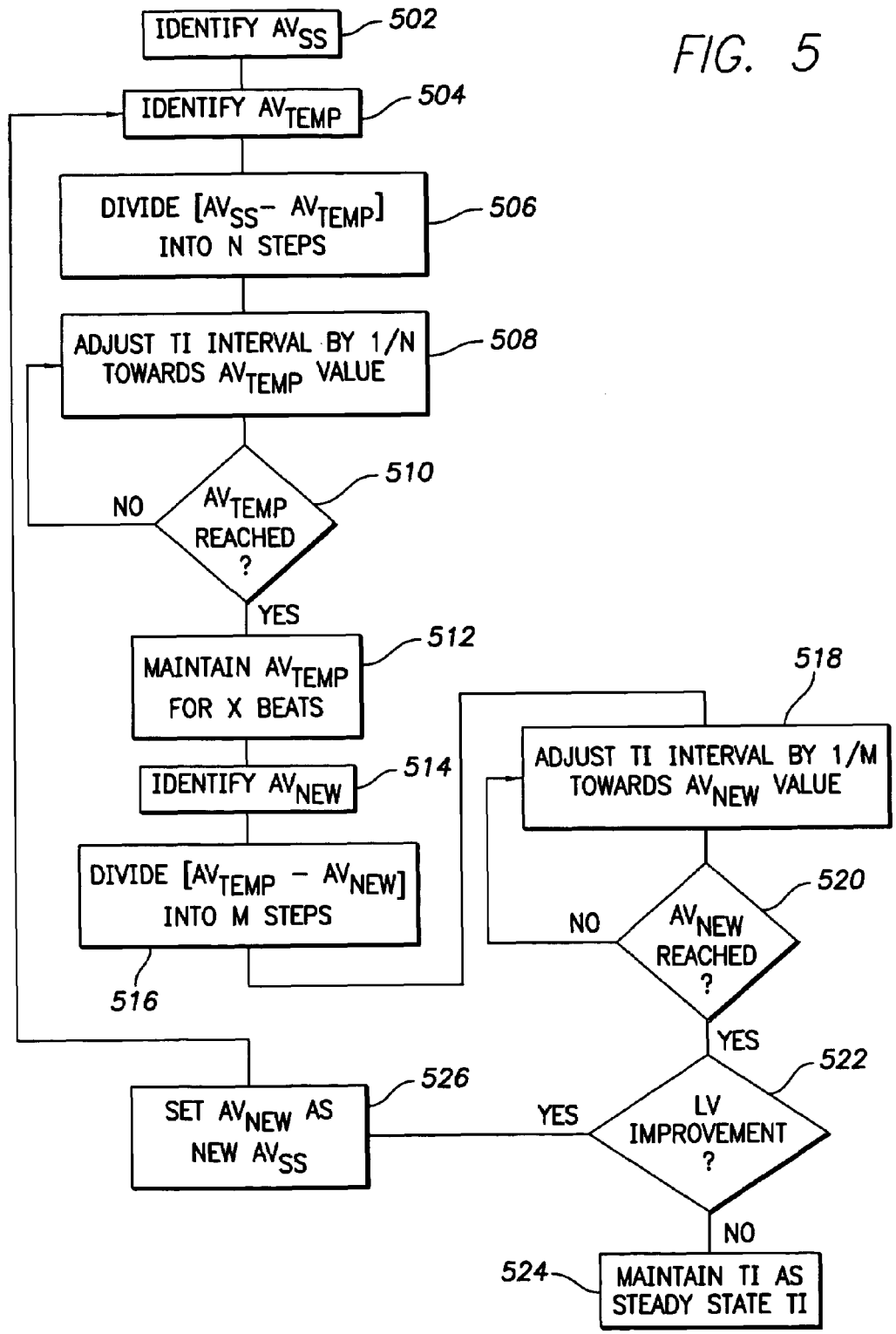
FIG. 5 is a flowchart illustrating with more specificity the high-level steps of FIG. 4.

With reference now to FIG. 5, the high level steps described above are more specifically carried out in terms of the following algorithm. Using AV delay as an example to illustrate one specific application, the method involves first identifying the steady state AV delay value $AV_{SS}$, at step 502. A first temporary value, $AV_{TEMP}$, is then identified, selected and programmed into the ICD memory, at step 504. The temporary delay value is of a level adequate to disturb the hemodynamic system. This value may be determined through data sensed by the physiologic sensors or monitors or manually by the physician prior to implantation of the ICD, or may simply be a scaled factor of the steady state value $AV_{SS}$. Additionally, analysis of echocardiograms may be performed to determine an appropriate $AV_{TEMP}$. Typically, the value of $AV_{TEMP}$ is selected from within fifty to seventy-five percent of the current steady-state value $AV_{SS}$.

Upon initiation of the algorithm, the ICD divides the difference between the steady state AV delay $AV_{SS}$ and the temporary delay $AV_{TEMP}$, into N steps, at step 506. The delay value is then incrementally altered, at step 508 (in this example, shortened) by one of the N steps until the pre-programmed temporary value $AV_{TEMP}$ is reached, at step 510. Once the value of $AV_{TEMP}$ is reached, the interval is maintained a predetermined number of beats, at step 512. Preferably, the AV delay change in each step is a consistent increment from between ten to fifty milliseconds, with each step occurring during periods ranging from one to three beats.

Figure 6A:
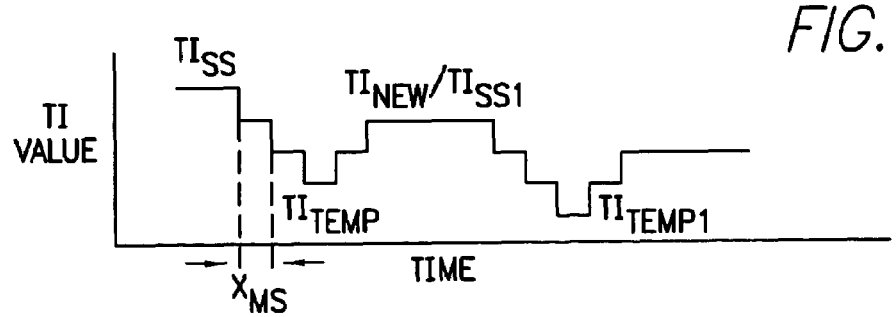
FIGS. 6a and 6b are graphs plotting timing interval value versus time to illustrate examples of timing interval sequences controlled by the method steps of FIG. 5.

FIG. 6a illustrates the sequence of timing interval changes in accordance with the steps illustrated in FIG. 5. In particular, the initial changes in the timing interval from $AV_{SS}$ to $AV_{TEMP}$ create a transient disturbance in the hemodynamic system that allows for adaptive control.

This initial transient disturbance in the hemodynamic steady state is important since it causes a significant decrease in end diastolic volume (EDV) for that cycle. In the next beat, the reduced filling resistance enables an increase in filling, but possibly not enough to remove damping blood in the right atrium (RA). If left at this level, venous pressure would likely increase.

With further reference to FIGS. 5 and 6a, to avoid an increase in venous pressure, once the dwell period for the temporary AV delay value $AV_{TEMP}$ has expired, the interval is again altered incrementally by a series of N steps. However, this sequence of steps lengthens the interval from $AV_{TEMP}$ back toward the original steady state value, and can return the AV delay value back to the initial steady state value $AV_{SS}$, or to a level within the range defined by the steady state AV delay, and the initial temporary value $AV_{TEMP}$. This is done by first determining a new steady state value, $AV_{NEW}$, at step 514, and dividing the difference between $AV_{NEW}$ and $AV_{TEMP}$ into M increments, at step 516. The AV delay is then incrementally altered by one of the interval increments, at step 518, and checked at step 520 to see if the value of $AV_{NEW}$ is reached. The incrementing and determining steps continue until $AV_{NEW}$ is reached. This new level, preferably within between ten to fifteen percent of the previous steady-state value $AV_{SS}$, is maintained for a predetermined number of beats to allow for hemodynamic data collection and analysis.

While in one embodiment, the transitions between $AV_{SS}$ and $AV_{TEMP}$, and between $AV_{TEMP}$ and $AV_{NEW}$ are carried out in steps, it will be apparent that the transition can be done by simply changing the value from the beginning value to the end value, without any intervening levels.

Several ways of collecting data for adaptive feedback are suitable for use in the method described herein. One exemplary method involves monitoring RA or RV pressure through the physiologic sensors. Either pressure gives an indication of venous pressure, which varies inversely with cardiac output. Thus, a decrease in RA pressure indicates an increase in cardiac output, evidencing an improvement in LV function, while an increase in RA pressure suggests a decrease in cardiac output, and a worsening condition.

If an improvement in left ventricular LV function is detected, at step 522, the steps described above are repeated, beginning with the new AV delay value $AV_{NEW}$, which is re-identified as $AV_{SS}$, at step 526. The timing interval is shortened over N steps until a new temporary transient value is reached, $AV_{TEMP2}$, at the previously described step 510. From this value, the interval is lengthened over M steps until a new value $AV_{NEW2}$ is reached, at step 520. Iterations in the process continue until no further improvement in LV function is detected at step 522. With no further improvement detected, the current AV delay interval is maintained as the new steady state value.

In an alternative embodiment, if an improvement is detected, the system maintains the AV delay value at $AV_{NEW}$, and uses that value as the steady state value until the need arises again to disturb the steady state. For example, the system may be programmed to periodically repeat the process, for example once per hour, once per day, once per week, etc. In yet another embodiment, the AV delay value is returned to the initial steady state value rather than to a new AV delay value.

Figure 6B:
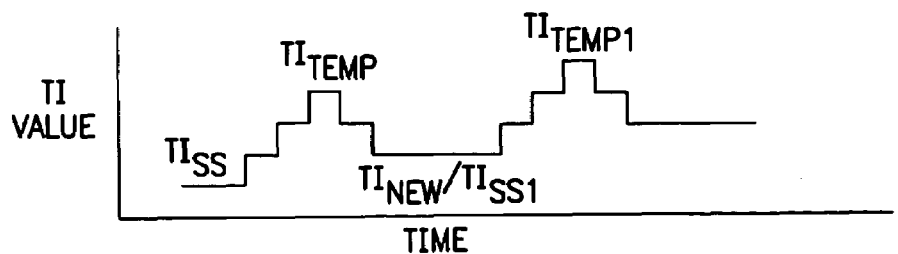

While the steps described above alter the AV delay by adaptively shortening the interval, a method that adaptively lengthens the interval may also be employed, depending on the application. Such a scheme is illustrated in FIG. 6b.

As noted above, AV delay is but one of several timing intervals that may be changed to effect a reduction in end diastolic volume for long-term changes in hemodynamic steady state. Another approach similar to the above process maintains the AV delay at a fixed value, and instead alters the timing interval between successive heart beats, or heart rate.

A variation in altering the heart rate interval to reduce end diastolic volume involves, in one illustrative embodiment, intentionally introducing premature ventricular contractions, or PVCs. PVC's occur when the ventricles beat prematurely before the normal electrical activation sequence of the heart has occurred. This may be accomplished in a straightforward manner for pacing applications utilizing biventricular schemes, as is often the case for cardiac resynchronization therapy.

Thus, similar to adaptively altering the AV delay interval as described above, the cycle-to-cycle ventricular event interval may be altered transiently, by introducing one or more PVCs to one or more cardiac cycles, to disturb the system and thereby shift the steady state conditions. The pattern for PVC injections may vary as the application dictates, but one example involves one PVC every N atrial beats for a predetermined number of cycles, or M paced PVC's for N atrial beats or paced bigeminy.

By disturbing the cardiovascular system and sympathetic reflex due to paced PVCs, the residual volume at end diastole is reduced. For left ventricular dysfunction with reserved eject fraction, this disturbance is helpful for reducing both left ventricular diastolic volume and pressure. By altering the parameters involved in defining the cardiac resynchronization therapy and the PVC interval, different hemodynamic effects may be achieved that are applicable to both diastolic and systolic heart failure.

Figure 7:
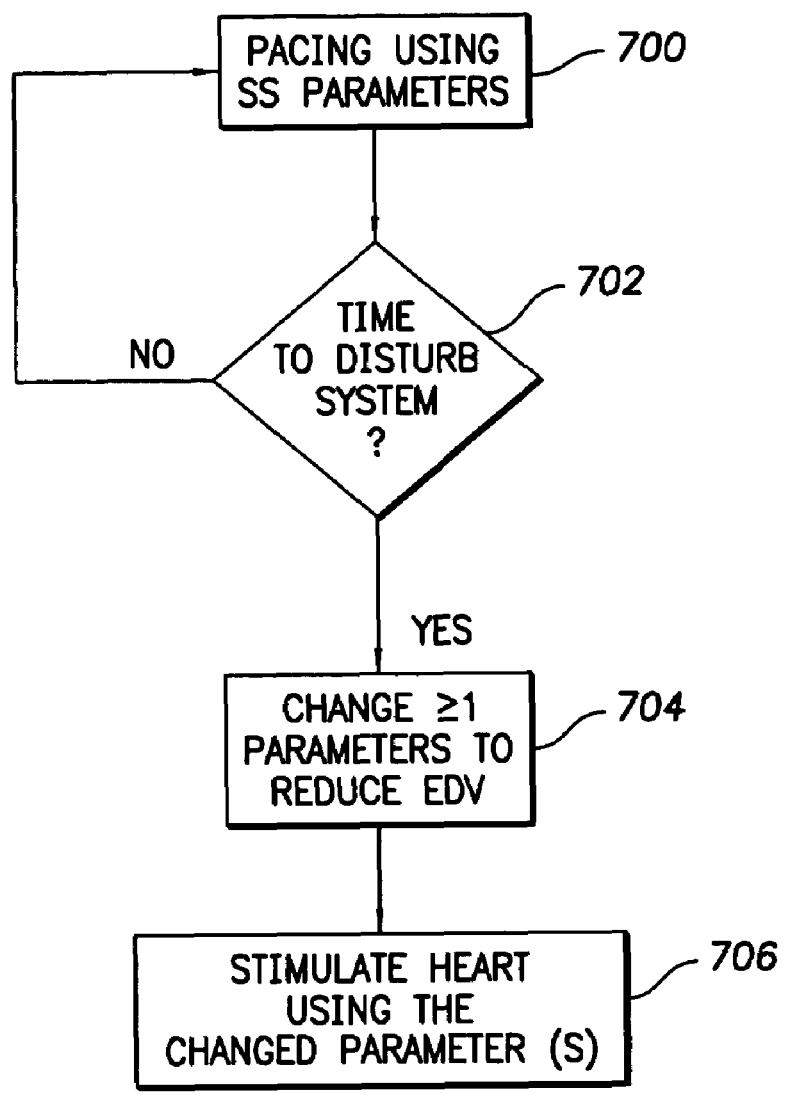
FIG. 7 is a flowchart depicting another illustrative embodiment of the method

Referring now to FIG. 7, an algorithm according to an alternate embodiment will be described. At step 700, operation begins with the system pacing the heart using the steady state pacing parameters. At query block 702, the system determines whether it is time to disturb the heart and alter the steady state. In one embodiment, this determination is made based on the time since the last disturbance to the system. For example, the algorithm may execute once per day. In another embodiment, a determination of cardiac performance may be carried out, such as measuring a surrogate for stroke volume or end diastolic volume, using impedance or pressure measurements as is well known. If it is not time to disturb the system, the operation returns back to step 700. On the other hand, if it is time to disturb the system, operation proceeds to step 704, and the system changes one or more operating parameters to disrupt the steady state, for example either shortening the AV delay value, increasing the heart rate, or injecting one or more PVCs over one or more cardiac cycles. At step 706, the system stimulates the heart using the changed parameter(s), preferably over a course of a number of cardiac cycles, or alternately for only a single cycle.

After using the modified parameter(s) to disturb the steady state, the system may revert back to the steady state parameters at step 700, or select one or more new parameters as described above in connection with FIGS. 6A and 6B.

Those skilled in the art will recognize the many benefits and advantages afforded by the adaptive timing interval method disclosed herein. Of significant importance is the initial transient disturbance brought about on the system by altering the timing interval to allow for a gradual adaptive shifting of the system hemodynamic parameters. Over time, this results in a shifting of the PV loop, thereby contributing to improved cardiac function, and reversing the effects of congestive heart failure.

While the invention has been particularly shown and described with reference to the preferred embodiments thereof, it will be understood by those skilled in the art that various changes in form and detail may be made therein without departing from the spirit and scope of the invention. For instance, while the method steps described herein note certain calculations and adjustments at certain times, the calculations and desired adjustments may be pre-programmed or handled in real-time depending on the application.

What is claimed is:

1. A method of treating a heart with an implantable cardiac stimulation device, the heart exhibiting initial steady state hemodynamic parameters, the method comprising:
    pacing the heart using a first set of pacing parameters comprising at least one cardiac pacing timing interval having an initial steady state value;
    disturbing the steady state hemodynamic parameters by altering the cardiac pacing timing interval from the initial steady state value to a temporary value for at least one cardiac cycle sufficient to reduce end diastolic volume for the at least one cardiac cycle; and
    adjusting the cardiac pacing timing interval by selecting a desired steady state value within a range defined by the initial steady state value and the temporary value, and changing the cardiac pacing timing interval from the temporary value to the desired steady state value, wherein the desired steady state value is different from the initial steady state value and the temporary value.

2. The method of claim 1 wherein adjusting the cardiac pacing timing interval comprises adaptively controlling the cardiac pacing timing interval for successive cardiac cycles to achieve a second set of hemodynamic parameters.

3. A method of treating the heart according to claim 1 wherein the cardiac pacing timing interval comprises at least one parameter from the group comprising:
    heart rate, atrio-ventricular (AV) delay, atrial interconduction (A-A) delay, ventricular interconduction delay (V-V), or ventricular-atrial (V-A) delay.

4. A method of treating the heart according to claim 3 wherein the heart rate cardiac pacing timing interval is defined by a plurality of ventricular events, at least one of the ventricular events comprising a premature ventricular contraction (PVC).

5. A method of treating the heart according to claim 1 wherein disturbing the steady state hemodynamic parameter comprises:
    selecting the temporary value; and
    incrementally adjusting the cardiac pacing timing interval value from the steady state value to the temporary value in a first series of steps over a predetermined period.

6. A method of treating the heart according to claim 5 wherein the first series of steps comprises a first programmed sequence of between two to ten steps.

7. A method of treating a heart according to claim 1 wherein the desired steady state value is maintained a predetermined number of cardiac cycles.

8. A method of treating a heart according to claim 1 wherein adjusting the cardiac pacing timing interval further comprises:
    detecting data indicative of cardiac function.

9. A method of treating a heart according to claim 8 and further comprising:
    repeating the disturbing and adjusting if an improvement in cardiac function is determined.

10. A method of treating a heart with an implantable cardiac stimulation device, the heart exhibiting initial steady state hemodynamic parameters, the method comprising:
    pacing the heart using a first set of pacing parameters comprising at least one cardiac pacing timing interval having an initial steady state value;
    disturbing the steady state hemodynamic parameters by altering the cardiac pacing timing interval from the initial steady state value to a temporary value for at least one cardiac cycle sufficient to reduce end diastolic volume for the at least one cardiac cycle;
    adjusting the cardiac pacing timing interval by selecting a desired steady state value within a range defined by the initial steady state value and the temporary value, and changing the cardiac pacing timing interval from the temporary value to the desired steady state value;
    adaptively controlling the cardiac pacing timing interval for successive cardiac cycles to achieve a second set of hemodynamic parameters; and
    maintaining the second set of hemodynamic parameters as a second set of steady state hemodynamic parameters.

11. A method of treating a heart with an implantable cardiac stimulation device, the heart exhibiting initial steady state hemodynamic parameters, the method comprising:
    pacing the heart using a first set of pacing parameters comprising at least one cardiac pacing timing interval having an initial steady state value;
    disturbing the steady state hemodynamic parameters by altering the cardiac pacing timing interval from the initial steady state value to a temporary value for at least one cardiac cycle sufficient to reduce end diastolic volume for the at least one cardiac cycle; and
    adjusting the cardiac pacing timing interval by selecting a desired steady state value within a range defined by the initial steady state value and the temporary value, and changing the cardiac pacing timing interval from the temporary value to the desired steady state value, wherein the cardiac pacing timing interval is changed from the temporary value to the desired steady state value in a series of steps over a predefined period.

12. An implantable cardiac stimulation device for treating a heart suffering from congestive heart failure, the device comprising:
    means for pacing the heart using a first set of pacing parameters comprising at least one cardiac pacing timing interval having an initial steady state value;
    means for disturbing steady state hemodynamic parameters of the heart comprising means for altering the cardiac pacing interval from the initial steady state value to a temporary value for at least one cardiac cycle sufficient to reduce end diastolic volume for that cycle; and
    means for adjusting the cardiac pacing interval by selecting a desired steady state value within the range defined by the initial steady state value and the temporary value, and changing the cardiac pacing timing interval from the temporary value to the desired steady state value, wherein the desired steady state value is different from the initial steady state value and the temporary value.

13. The implantable cardiac stimulation device of claim 12 wherein the means for altering a cardiac pacing interval comprises means for altering one of heart rate, atrio-ventricular (AV) delay, atrial interconduction (A-A) delay, ventricular interconduction delay (V-V), or ventricular-atrial (V-A) delay.

14. An implantable cardiac stimulation device for treating a heart suffering from congestive heart failure, the device comprising:
   means for pacing the heart using a first set of pacing parameters comprising at least one cardiac pacing timing interval having an initial steady state value;
   means for disturbing steady state hemodynamic parameters of the heart comprising means for altering the cardiac pacing interval from the initial steady state value to a temporary value for at least one cardiac cycle sufficient to reduce end diastolic volume for that cycle; and
   means for adjusting the cardiac pacing interval by selecting a desired steady state value within the range defined by the initial steady state value and the temporary value, and changing the cardiac pacing timing interval from the temporary value to the desired steady state value;
   wherein the means for disturbing comprises means for selecting the temporary timing interval value, and means for incrementally adjusting the cardiac pacing interval value from the steady state value to the temporary value.

15. A method of pacing a heart comprising:
   pacing the heart using a first set of pacing parameters comprising at least one cardiac pacing timing interval having an initial steady state value;
   altering the cardiac pacing timing interval from the initial steady state value to a temporary value for at least one cardiac cycle, wherein the altering is sufficient to reduce end diastolic volume for the at least one cardiac cycle; and
   adjusting the cardiac pacing timing interval by selecting a desired steady state value within the range defined by the initial steady state value and the temporary value, and changing the cardiac pacing timing interval from the temporary value to the desired steady state value, wherein the desired steady state value is different from the initial steady state value and the temporary value.

16. An implantable cardiac stimulation system comprising:
   at least one lead adapted for implant within a patient and comprising at least one electrode connected to the lead for electrical contact with the patient's heart;
   an implantable cardiac stimulation device connected to the at least one lead and comprising a controller and a pulse generator, wherein the controller is operative to control the pulse generator to pace the heart using a first set of pacing parameters comprising at least one cardiac pacing timing interval having an initial steady state value, to disturb the steady state hemodynamic parameters by altering the cardiac pacing timing interval from the initial steady state value to a temporary value for at least one cardiac cycle sufficient to reduce end diastolic volume for the at least one cardiac cycle, and to adjust the cardiac pacing timing interval by selecting a desired steady state value within the range defined by the initial steady state value and the temporary value, and changing the cardiac pacing timing interval from the temporary value to the desired steady state value, wherein the desired steady state value is different from the initial steady state value and the temporary value.

17. The implantable cardiac stimulation system of claim 16 wherein the controller is operative to alter one of heart rate, atrio-ventricular (AV) delay, atrial interconduction (A-A) delay, ventricular interconduction delay (V-V), or ventricular-atrial (V-A) delay.

18. The implantable cardiac stimulation system of claim 16 wherein the controller is operative to select the temporary value, and to incrementally adjust the cardiac pacing interval value from the steady state value to the temporary value.

* * * * *